United States Patent [19]

Bryce-Smith

[11] Patent Number: 5,622,724
[45] Date of Patent: Apr. 22, 1997

[54] SPRAY PREPARATION FOR TREATING SYMPTOMS OF THE COMMON COLD CONTAINING UNCHELATED IONIC ZINC COMPOUNDS

[75] Inventor: Derek Bryce-Smith, Reading, England

[73] Assignee: Kappa Pharmaceuticals Limited, Reading, England

[21] Appl. No.: 112,570

[22] Filed: Aug. 26, 1993

Related U.S. Application Data

[63] Continuation of Ser. No. 874,756, Apr. 27, 1992, abandoned, which is a continuation of Ser. No. 799,423, Nov. 25, 1991, abandoned, which is a continuation of Ser. No. 474,273, Feb. 2, 1990, abandoned.

[30] Foreign Application Priority Data

Feb. 2, 1989 [GB] United Kingdom .................. 8902300

[51] Int. Cl.$^6$ .................................................. A61K 33/32
[52] U.S. Cl. ........................... 424/641; 424/642; 424/43; 424/45; 514/494
[58] Field of Search ............................. 424/641, 43, 45, 424/642; 514/494

[56] References Cited

U.S. PATENT DOCUMENTS

| | | |
|---|---|---|
| 3,852,432 | 12/1974 | Henkin . |
| 4,255,419 | 3/1981 | Leopold . |
| 4,292,324 | 9/1981 | Jonsson et al. . |
| 4,503,070 | 3/1985 | Eby . |
| 4,814,163 | 3/1989 | Barth . |
| 4,814,164 | 3/1989 | Barth et al. . |
| 4,946,688 | 8/1990 | Fahim . |
| 4,956,385 | 9/1990 | Eby, III . |
| 5,002,970 | 3/1991 | Eby, III . |
| 5,409,905 | 4/1995 | Eby, III ..................................... 514/23 |

*Primary Examiner*—Theodore J. Criares
*Assistant Examiner*—M. Moezie
*Attorney, Agent, or Firm*—Oblon, Spivak, McClelland, Maier & Neustadt, P.C.

[57] ABSTRACT

The present invention provides a simple, cheap and efficient cure for the common cold, and comprises a nasal spray of a dilute solution of substantially unchelated zinc ion, especially zinc sulphate and/or zinc chloride.

8 Claims, 4 Drawing Sheets

SPRAY PREPARATION FOR TREATING SYMPTOMS OF THE COMMON COLD CONTAINING UNCHELATED IONIC ZINC COMPOUNDS

This application is a continuation of U.S. application Ser. No. 07/874,756 filed Apr. 27, 1992, now abandoned, which is a continuation of U.S. application Ser. No. 07/799,423 filed Nov. 25, 1991, now abandoned, which is a continuation of U.S. application Ser. No. 07/474,273 filed Feb. 2, 1990, now abandoned.

BACKGROUND OF THE INVENTION

The present invention relates to preparations of zinc compounds for use in the treatment and/or prophylaxis of the common cold.

Zinc and its compounds have long been recognized as possessing certain therapeutic functions. Particularly well recognized are benefits as astringents and wound healing agents. The latter use tends to be restricted to zinc chloride and zinc sulphate, zinc chloride being of use for application to foul-smelling wounds and ulcers, while zinc sulphate is given internally to promote healing.

Zinc sulphate has also proven beneficial in the treatment of acrodermatitis enteropathica and, in common with zinc acetate, is used in eye drops, optionally in combination with adrenaline or boric acid (no longer medically recommended), to relieve chronic inflammation of the cornea in conjunctivitis. Together with zinc chloride, zinc sulphate is also used as an astringent mouth wash, and was formerly used as a reflex emetic, owing to its irritant and adverse effects on the gastrointestinal mucosae (of Merck Index, entry 9966).

Zinc compounds have also been used, with varying degrees of success, in the treatment of acne, aphthous ulcers, coeliac disease, cystic fibrosis, senile dementia, furunculosis, gastric ulcers, hyperthyroidism, leg ulcers, porphyria, rheumatoid arthritis, sickle-cell anaemia and ulcerative colitis.

Approximately 40% of common colds are caused by rhinovirus infections. The precise mechanism of action is not known, although zinc has been shown to inhibit virion maturation by blocking cleavage of the large polypeptide which is the primary transcription product of the vital genome. This effect may be caused by zinc acting as a protease inhibitor or by binding to and stabilizing regions of the precursor polypeptides. The latter possibility is supported by the observation that the polypeptides accumulating in the infected cell, in the presence of zinc, are primarily those containing coat protein sequences. Zinc has been shown to bind readily to purified rhinovirus, preventing normal crystallization.

In addition, rhinoviruses passaged in the presence of zinc (zinc resistant mutants) have been shown to display altered antigens. This suggests that zinc may affect the in vitro pathogenicity of the virus by making virions more susceptible to antibody attack as well as reducing the amounts of transmissible virus released.

Of two reports on the effects of zinc (see below), administered orally, on rhinovirus infections, one involved infecting healthy volunteers with purified virus, while the other involved subjects with naturally acquired infections. Both examined the effects of orally administered zinc gluconate (lozenges with 23 mg Zn) on symptom severity. Significant effects on duration of symptoms, overall symptom severity and the amount of nasal secretion were detected.

Accordingly, investigation of zinc compounds has centered upon their possible use to inhibit or cure the common cold. For example, Eby, et al. (Antimicrobial Agents and Chemotherapy [1984], 25, [1], pp 20–24) disclose the use of zinc gluconate lozenges in the treatment of the common cold. Their study indicated that, after 7 days, 86% of zinc-treated subjects were asymptomatic, compared with only 46% of placebo-treated subjects. However, the observers noted "objectionable taste and mouth irritation" in the patients.

With one exception, attempts to duplicate Eby's results have been uniformly negative. Eby's original results were questioned, given that, as noted above, zinc ions taste metallic and cause a sore mouth and nausea in the patient. In addition, the Merck Index (10th Edition) notes zinc sulphate as being irritating to both skin and mucous membranes, and states that a solution of zinc sulphate has a pH of 4.5. For a review of results obtained with zinc gluconate, see Antimicrobial Agents and Chemotherapy (1988), 32, pp. 605–7.

In U.S. Pat. No. 4,503,070, Eby discloses the use of nasal sprays of zinc solutions to treat the common cold. However, not only is such use unsupported by the description, but the concentrations to which such sprays are limited are of an order of magnitude so large as to cause substantial discomfort to the patient. Prior art is also described therein comprising the use of suspensions of zinc borate. Such suspensions provide high quantities of zinc but are essentially ineffective and, in addition, the particles may block the alveoli of the lungs, which can ultimately give rise to a condition similar to emphysema.

In a later unpublished paper, the conclusions of which were, however, published in a letter to the Lancet, Eby et al. established that a zinc gluconate nasal spray (10 mM) was only marginally effective, and was not worth following up. Also, DE 3431727 A1, filed in 1984, discloses a nasal spray comprising zinc gluconate in a 2% solution. No results are provided, and the applicant failed to continue with the application.

In two other papers in Antimicrobial Agents and Chemotherapy ([1987], 31, 1183–7 and 1263–5), it was established that neither zinc gluconate nor zinc acetate provided a therapeutically useful treatment of rhinovirus colds.

SUMMARY OF THE INVENTION

It is an object of the present invention to provide a treatment for the common cold which is easy and cheap to prepare.

It is a further object of the present invention to provide a treatment for the common cold which is easy and safe to administer.

A solution of substantially unchelated zinc ions, administered in the form of a spray to the respiratory tract, nasally or orally, is effective in the treatment or prophylaxis of the common cold.

Thus, there is provided a method for the treatment or prophylaxis of the common cold, in a subject in need thereof, comprising administering a non-toxic solution of substantially unchelated zinc ions in the form of a spray to the respiratory tract of the subject, especially by the nasal route.

There is also provided the use of an ionic zinc compound in the manufacture of a medicament for the treatment or prophylaxis of the common cold, the medicament comprising a solution containing substantially unchelated zinc.

There is yet further provided an aerosol dispensing device, preferably hand-held, comprising a reservoir of a, preferably aqueous, solution containing substantially unchelated ionic zinc, the device being adapted to dispense a spray of the solution into a human nostril.

DETAILED DESCRIPTION OF THE INVENTION

Figure 1:
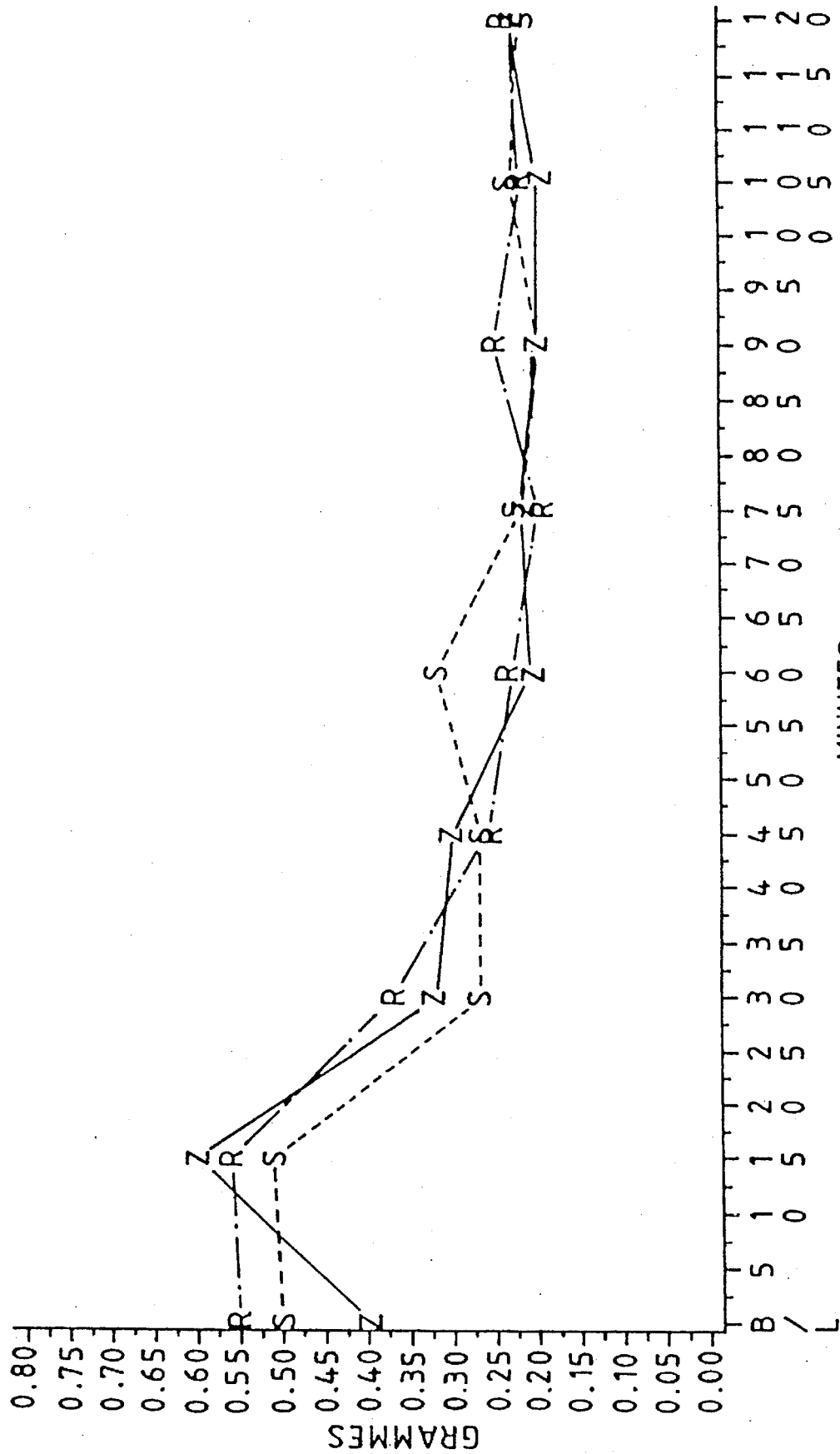
FIG. 1 is a graphic representation of the effects of a spray of the invention, together with 2 controls, on subjects having varying degrees of cold over an initial period of 2 hours.

The term "ionic", as used herein, relates to suitable zinc compounds capable of use to give solutions of ionic zinc.

By the term "common cold" is meant that condition generally associated with the term, including any or all symptoms thereof, such as headaches, sore throat, runny and/or congested nose and coughs. In particular, the preparations of the invention are suitable for the treatment of an infection by a virus generally recognized as causing, or being associated with, the symptoms of a common cold. Most common of the types of virus associated with the common cold is the group known as the Rhinoviridae, particularly HRV-2.

The terms "treatment" and "prophylaxis" are used in a broad sense, and extend from symptomatic relief to cure of the infection to general preventative therapy, especially in winter, or for particularly prone individuals.

While it is believed that the preparations of the invention are actually virostatic or viricidal, it will be appreciated that this is not known for certain, and it is possible that only symptomatic relief is obtained. Particularly, the preparations of the invention are suitable for use any time from when the subject first notices any signs of a cold until the symptoms have cleared up. In fact, in some cases, such as for persistent sufferers, or where individually desired, it may be appropriate to continue treatment indefinitely, in the absence of contraindications. In general, best results seem to be obtained when treatment is commenced immediately there is any suspicion of a cold. Several doses in rapid succession, such as between 2 and 10, preferably about 4 to 6 over an hour, are frequently sufficient to overcome even the most severe onset. If symptoms persist after this initial period, it is generally recommended to reduce frequency of dosing to the levels described hereunder.

By "substantially unchelated" is meant any solution of zinc ion wherein a majority of the zinc is in free solution. It will be appreciated that, for medical use, solutions of ionic zinc are necessary. For this purpose, any compound may be used that releases zinc ion in solution. Certain compounds may oridinarily provide solutions of chelated zinc, but may still be usable, provided that the solvent chosen effectively prevents chelation, or that the chelating moiety is somehow prevented from chelating zinc. It may also be the case that the final solution contains amounts of a zinc chelator. This may be permissible, provided that the chelator is present in less than, preferably very much less than, stoichiometric amounts. In such cases, the amount of chelated zinc should be subtracted from the total before calculating dosages.

Thus, there is a contrast with the art, such as the gluconate, where the zinc is bound at least partially with a stoichiometric quantity of chelator. It was previously considered that solutions of free ionic zinc could not be administered at all, and especially not in effective doses, without giving rise to substantial irritation and other adverse side effects. This is not the case, and patients treated with the sprays of the invention report no bad taste or other side effects.

By "solution" is meant any solution of ionic zinc suitable to provide free zinc ions on administration. Although the invention extends to solutions of zinc capable of yielding free zinc ion but which contain zinc in another form, it is generally the case that preferred solutions contain substantially unchelated zinc ion.

Thus, despite the strong contraindications in the art, it has been found that it is possible to use ionic zinc solutions in low enough concentrations that no irritation is caused, but in high enough concentrations to be effective. In fact, zinc compounds, especially zinc sulphate, are only recommended for clinical use in concentrations of less than 0.25%. The sprays of the invention are effective at concentrations of 0.1% or lower, whereas those solutions, including sprays, described in the art are around 2%, and have not even been proven effective.

Relief of symptoms, such as nasal discharge, is often virtually instantaneous (frequently within minutes of administration), it frequently being possible to abort a cold altogether if caught early enough. A cure, or substantial relief of symptoms, may frequently be effected even during substantial attacks.

In treatment, it is generally preferred to administer the spray via the nasal cavity, although severe symptoms may benefit from application via both nasal and oral cavities.

Efficacy is probably also enhanced by the affinity of zinc ions for mucous tissues. Thus, zinc ion is still present in the affected areas for periods of up to several hours after administration.

A particular advantage of the invention is that considerably less zinc compound, in terms of orders of magnitude, is required for efficacy, and no irritation, metallic taste or other undesirable side-effects are observed. Further, the solutions are remarkably effective, in contrast to the ambivalent art.

In addition, the solutions of the invention are desirably sufficiently dilute that there is no problem with acidity. A 0.1% solution of zinc sulphate heptahydrate in demineralized water typically has a pH of 5.1, for example, rising to about 5.7 after boiling to drive off carbon dioxide. This is similar to unpolluted rainwater.

Particularly good results have been obtained with zinc sulphate, although other ionic zinc compounds can be used, especially the chloride. In general, suitable anions are those allowing free dissociation in solution, that is, which do not chelate the zinc ion. Those compounds of low solubility, or which are only soluble with difficulty, may be less convenient for use, but are not excluded from the invention provided that an effective concentration of zinc may be obtained. Generally preferred compounds are salts of the mineral acids. Inorganic or simple organic compounds, such as zinc acetate, are generally preferable, but compounds which are capable of chelating zinc, such as the gluconate or citrate, should be avoided, unless in sufficiently small quantities.

It will also be appreciated that a compound dissolved in a solution of another compound will not necessarily yield a solution exhibiting the expected characteristics. For example, zinc chloride dissolved in a carbonate solution is likely to precipitate zinc carbonate, thereby reducing or eliminating zinc in solution.

The solvent used to dissolve the ionic zinc compound may be selected from any that is physiologically acceptable. Zinc sulphate, for example, is virtually insoluble in alcohol, but freely soluble in water, while zinc chloride is soluble in either. Indeed, a direct aqueous solution of the compound forms a preferred embodiment. However, other solutions are equally preferred, such as those based on saline and/or aqueous glycerol, or other mixtures suitable for nasal administration.

In tests, an aqueous solution of zinc sulphate has proven particularly effective, while zinc sulphate in saline is apparently not quite so effective, although test parameters varied somewhat. In particular, stage of the cold appears to be of significance with regard to efficacy, with colds only treated at later stages responding less well. However, this tallies well with zinc affecting the virus directly, as the virus will be wider spread at later stages of infection while, at earlier stages, there is a good chance of the virus still being localized in the nasal mucosae, with treatment effectively pre-emptying further replication. The cold is thereby caught early, and subsequent treatment of symptoms is unnecessary, as the subject is no longer infected.

The solutions used in accordance with the invention may also contain other ingredients that may be considered desirable, provided that these do not give rise to unacceptable levels of chelation. Such ingredients include, for example, buffering agents, flavor and odor enhancing agents, surface active agents, dispersing agents, decongestants and the like. The solutions for use in accordance with the invention may also contain, or be combined with, other medications suitable for administration by nasal spray, such as antimicrobial agents and antihistamines.

One preferred preparation contains about 0.1% menthol and about 3% ethanol (to dissolve the menthol). Such a formulation is preferred for the reason that a straight solution of zinc is virtually unnoticeable, especially when the patient suffers nasal discharge, and methanol, or another suitable compound, such as camphor, serves to make the patient aware of the presence of the solution.

The solutions of the invention may contain the ionic zinc compound in any suitable concentration. However, it is generally preferable to administer the compound in a concentration of between 0.01 and 1%, with 0.05 to 0.3% being particularly preferred. Solutions in excess of approximately 1% are increasingly liable to cause some irritation of mucous membranes.

The solution of the invention is preferably administered in doses of about 0.05 to 0.5 ml, more preferably 0.2 ml, per nostril. Administration is as often as required, but two doses per nostril at approximately six-hourly intervals has proven effective. Other regimes will be clear to those skilled in the art.

If the subject has a runny or blocked nose, it is generally recommended that they blow their nose before administration, to facilitate access of the solution to the mucosae. Inhaling during spraying is also recommended.

The solutions of the invention may be prepared in any suitable manner. In general, this will involve no more than the dissolution of the compound in the solvent. This will usually be at ambient or elevated temperature, and under aseptic conditions.

Suitable aerosol dispensers for use in accordance with the invention will be apparent to those skilled in the art, and may vary from simple devices analogous to perfume dispensers to pressurized spray cans and even complex apparatus such as might be used in hospitals.

Whichever device is used it is generally preferable that it comprises some kind of dosimeter to control the amount of solution administered in one go. A preferred device, which corresponds to a perfume dispenser with a nozzle, effectively incorporates such a dosimeter without any specialized adaptation being necessary, the limit stop of the depressable spray head fixing the maximum single amount of solution dispensable at once.

Specially developed spray devices may be made, but it is generally preferable to provide a simple hand-held device comprising a reservoir of the zinc solution.

Suitable means for dispersing the spray, preferably in aerosol form, are then provided. Examples include devices employing pressurized gas forced across the opening of a tube leading into the reservoir to create an aerosol, and press-button type devices wherein the button, when pressed, creates pressure on the surface of the liquid in the reservoir, forcing it up through a tube and through a fine nozzle to disperse the solution into an aerosol spray.

It is generally preferable that air forms the aerosol propellant, but any suitable propellant may be used.

The following Examples are for illustration only, and are not to be construed as limiting the invention in any way.

EXAMPLE 1

A randomized, single (Investigator) blind, parallel group, investigative, clinical study to assess the effects of a zinc sulphate containing nasal spray on symptoms associated with upper respiratory tract infections was performed, in particular to assess the effects of a zinc sulphate containing nasal spray on the symptoms of acute upper respiratory tract infections, with emphasis on the nasal symptoms of congestion and secretion.

The effects of a zinc sulphate containing nasal spray were investigated and compared with those of both the nasal spray vehicle without zinc sulphate and also a commercially available anti-secretory agent ("Rinatec" [Trade Mark of Boehringer Ingelheim Ltd.]—ipratropium bromide) in the treatment of symptoms associated with acute upper respiratory tract infections.

Zinc was formulated in a normal saline vehicle as $ZnSO_4$ (heptahydrate) (0.1% w/v).

The spray of the invention and the normal saline control were identically packaged in 15 ml clear glass containers equipped with a metered dose spray attachment.

Rinatec was presented in the commercially available pack, a 10 ml metered dose inhaler with nasal applicator.

The study was conducted under the cover of a U.K. Department of Health Clinical Trial Exemption Certificate.

Symptom Scoring

The subjects recorded the severity of their nasal congestion and secretions on various scales.

The congestion scale ran from "nose feels extremely blocked" at one end to "nose feels extremely clear" at the other, and the secretion scale ran from "nose feels extremely runny" at one end to "nose feels extremely dry" at the other end.

The subjects also scored the extent of relief from congestion and secretion on a nominal scale.

Amongst other standard considerations, subjects who produced less than 100 mg nasal secretion during a preliminary 15 minute assessment were excluded from the trial, as were those who had had symptoms for more than 96, or less than 6, hours.

Protocol

In a preliminary 120 minute assessment of secretion weight in the laboratory, a series of tissues (preweighed, numbered and in plastic bags) was provided, and subjects blew their noses at 15 minute intervals and the used tissues plus bag weighed.

The subjects were allocated a test medication according to a stratification and randomization code, and a single dose of the assigned medication administered.

The subjects received 2 sprays into each nostril while sitting erect, representing a dose of 400 μl (400 μg) zinc sulphate or 100 μl (40 μg) ipratropium bromide. The spray was administered with the applicator tip held just below the nostril, and not inserted into the nostril.

Fifteen minutes post-administration, subjects blew their noses into a preweighed tissue.

Fifteen minutes later, the subjects blew their noses into another tissue, assessed their congestion and secretion on the interval scales.

This regime (secretion assessments every 15 minutes, with nasal congestion and secretion assessments every 30 minutes) was continued until 120 minutes post-administration.

While in the laboratory, the subjects were also asked every 30 minutes whether they had experienced any unpleasant effects.

The subjects were then provided with a 4-day supply of test medication and a symptom/compliance diary for the remainder of the trial and, in an everyday environment, scored their individual symptoms at the beginning and end of each day over the 4 day period, recording the number of doses of test product taken each day.

Subjects applied 2 sprays per nostril (in the manner described above) as required, while symptoms persisted, to a maximum of 4 doses per day, and returned after 4 days with diary and unused test product.

TABLE 1

| | Results Length of Cold before Trial | | |
|---|---|---|---|
| | Saline + zinc | Saline | Rinatec |
| 1–2 days | 15 | 12 | 14 |
| 2–4 days | 15 | 18 | 17 |

In the accompanying FIG. 1, secretion weights over the first 120 minutes are shown (Z—saline/$ZnSO_4$, S—saline, R—Rinatec). It can be seen that, overall, there is no substantive difference between treatments at this stage.

Figure 2:
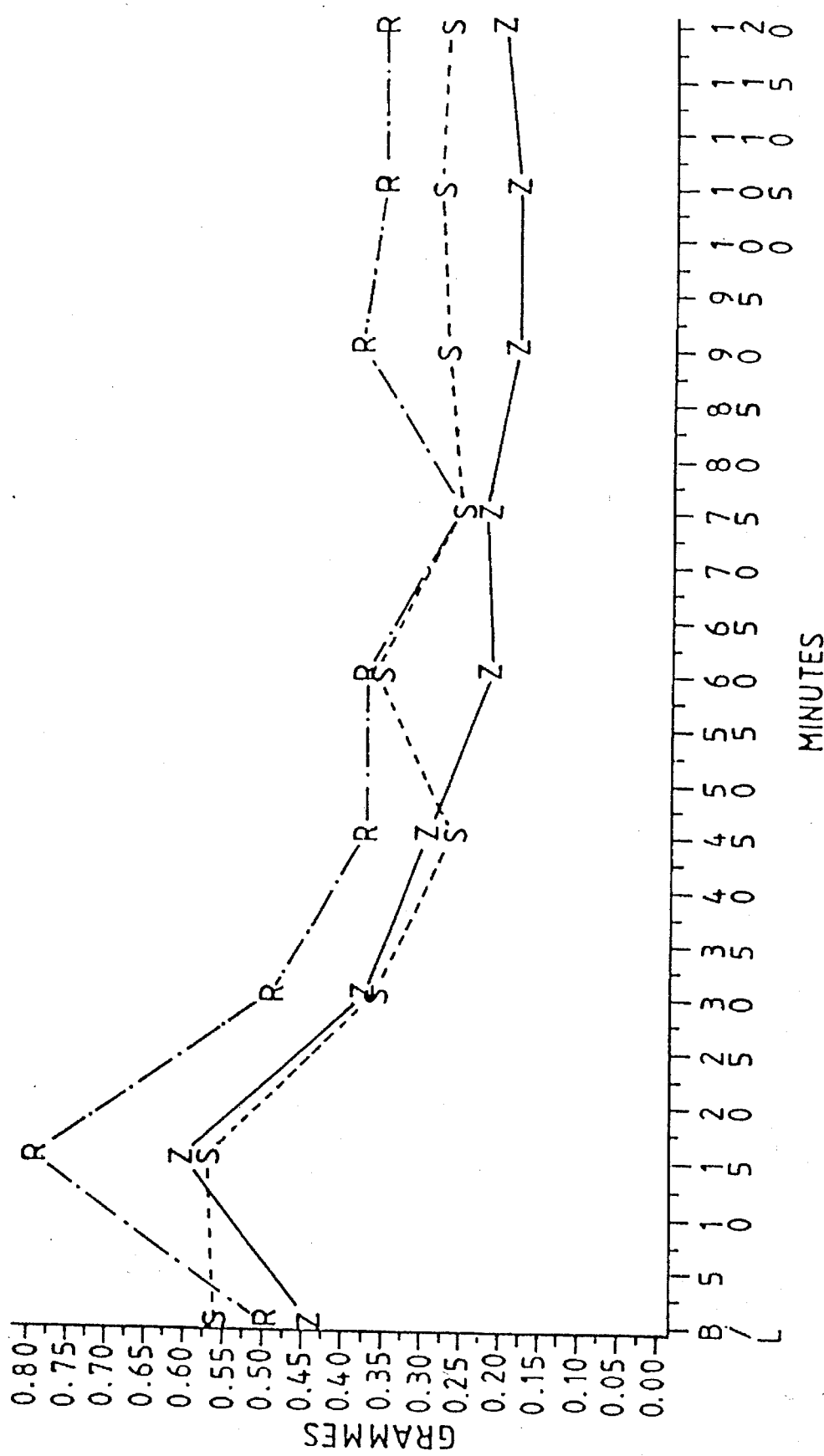
FIG. 2 is a graphic representation of the effects of a spray of the invention, together with 2 controls, on subjects having colds for 1–2 days, over an initial period of 2 hours.

However, in the accompanying FIG. 2, secretion weights for subjects having colds of only 1–2 days duration are shown, and it is clear that the spray of the invention exhibits a significant advantage.

Figure 3:
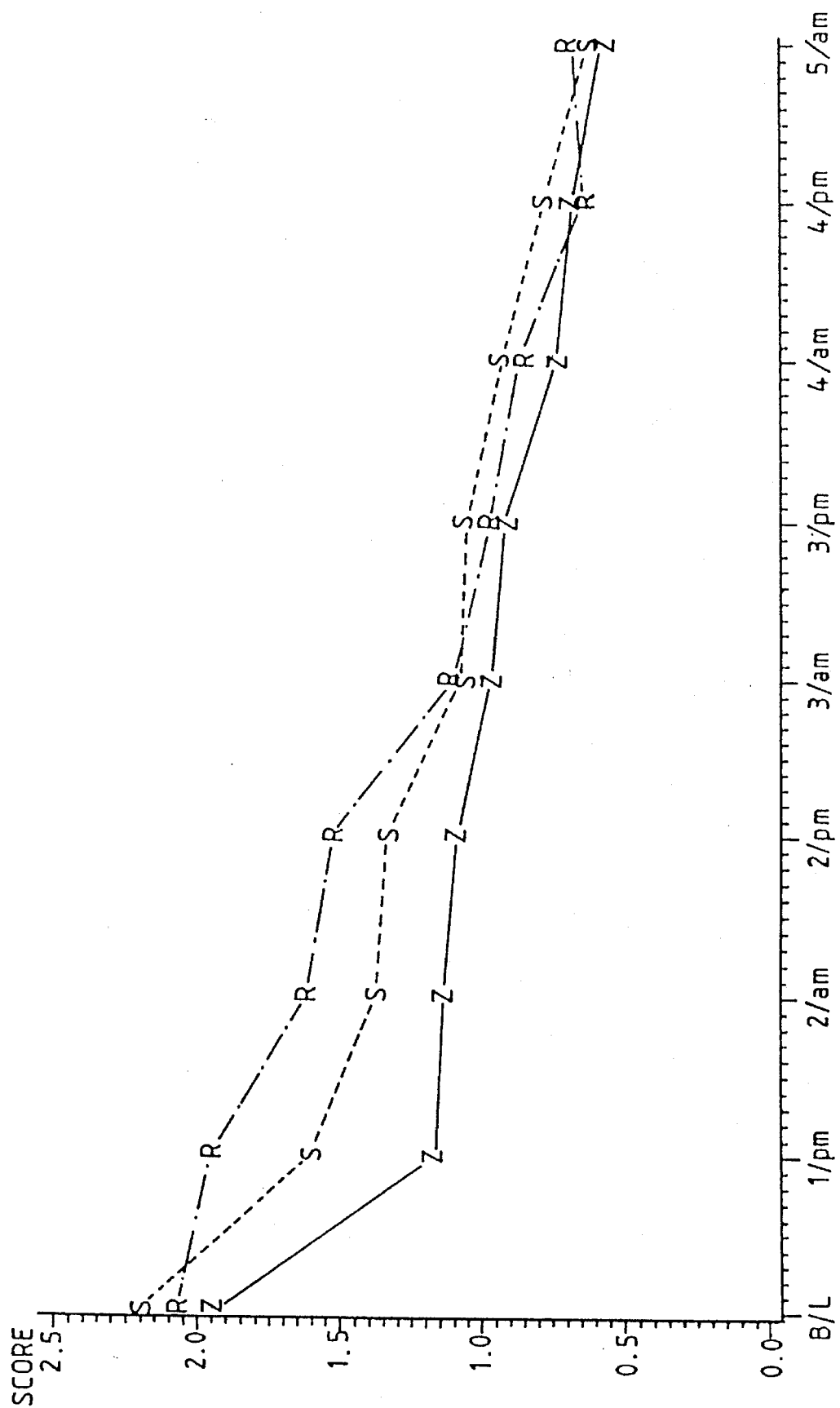
FIGS. 3 and 4 are graphic representations of the effects of a spray of the invention, together with 2 controls, on subjects having varying degrees of cold over a period of several days.
Figure 4:
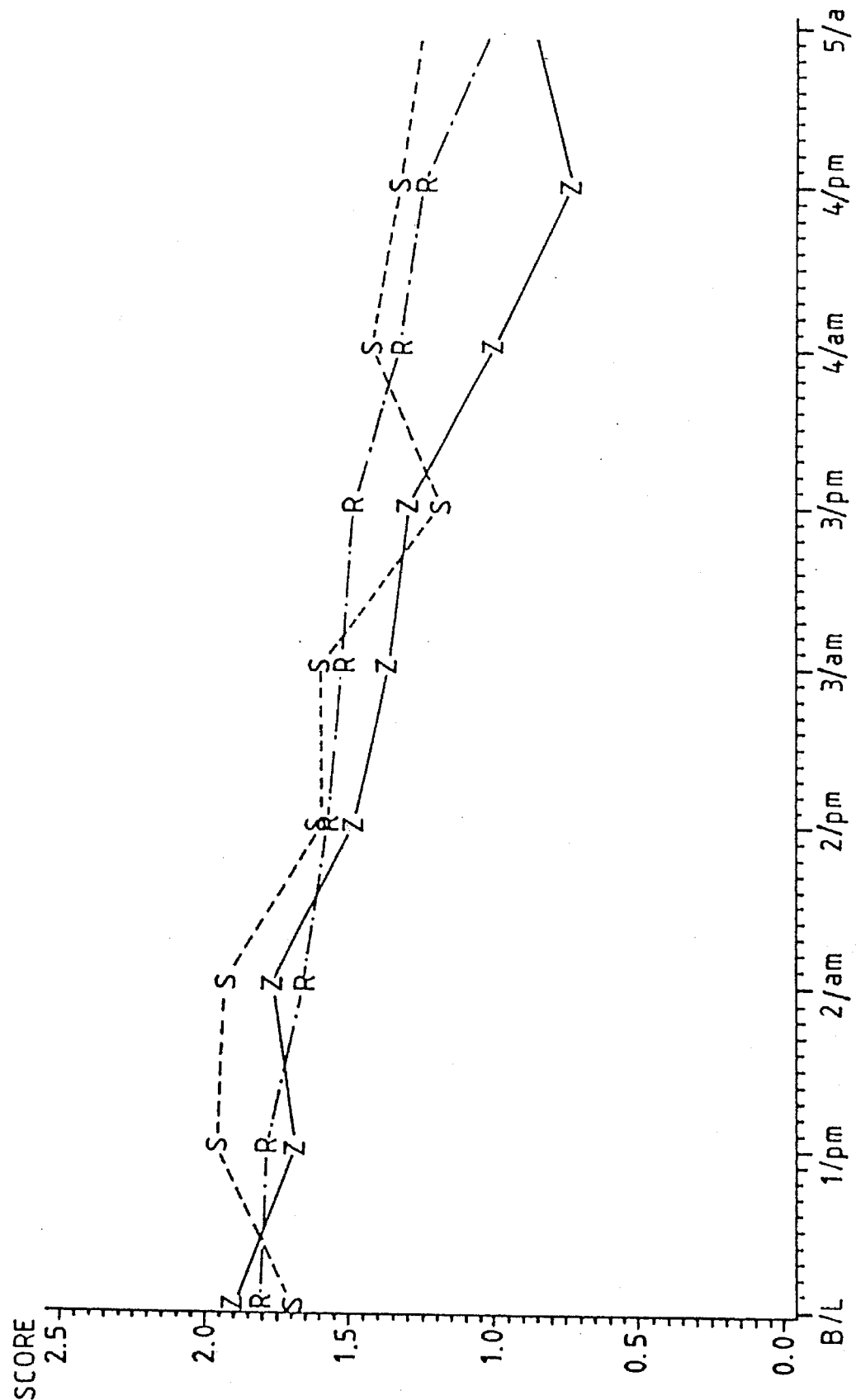

FIGS. 3 and 4 graphically represent the results of Tables 2 and 3 below, showing progress of colds over the 4-day trial period:

TABLE 2

| | | RUNNY NOSE DIARY FREQUENCY COUNTS | | | | | | | | | | | | | | |
|---|---|---|---|---|---|---|---|---|---|---|---|---|---|---|---|---|
| | | Saline + zinc score | | | | | Saline score | | | | | Rinatec score | | | | |
| Day | Time | 0 | 1 | 2 | 3 | 4 | 0 | 1 | 2 | 3 | 4 | 0 | 1 | 2 | 3 | 4 |
| 1 | am | 2 | 5 | 17 | 5 | 1 | 1 | 3 | 16 | 9 | 1 | 0 | 7 | 14 | 9 | 0 |
|   | pm | 6 | 10 | 6 | 2 | 1 | 3 | 9 | 0 | 5 | 0 | 2 | 6 | 7 | 7 |   |
| 2 | am | 6 | 10 | 7 | 1 | 0 | 7 | 7 | 9 | 4 | 0 | 2 | 9 | 8 | 4 |   |
|   | pm | 5 | 14 | 3 | 2 | 0 | 6 | 9 | 10 | 1 | 1 | 1 | 12 | 7 | 3 |   |
| 3 | am | 9 | 8 | 6 | 1 | 0 | 7 | 12 | 7 | 1 | 0 | 4 | 14 | 4 | 1 |   |
|   | pm | 6 | 13 | 4 | 0 | 0 | 6 | 15 | 5 | 1 | 0 | 5 | 14 | 4 | 0 |   |
| 4 | am | 9 | 10 | 3 | 0 | 0 | 8 | 10 | 6 | 0 | 0 | 9 | 8 | 4 | 1 |   |
|   | pm | 10 | 8 | 3 | 0 | 0 | 13 | 1 | 8 | 0 | 0 | 11 | 8 | 3 | 0 |   |
| 5 | am | 12 | 6 | 3 | 0 | 0 | 11 | 7 | 3 | 0 | 0 | 9 | 10 | 2 | 0 |   |

TABLE 3

| | | BLOCKED NOSE DIARY FREQUENCY COUNTS | | | | | | | | | | | | | | |
|---|---|---|---|---|---|---|---|---|---|---|---|---|---|---|---|---|
| | | Saline + Zinc score | | | | | Saline score | | | | | Rinatec score | | | | |
| Day | Time | 0 | 1 | 2 | 3 | 4 | 0 | 1 | 2 | 3 | 4 | 0 | 1 | 2 | 3 | 4 |
| 1 | am | 2 | 6 | 15 | 7 | 0 | 3 | 8 | 14 | 5 | 0 | 1 | 10 | 15 | 4 | 1 |
|   | pm | 4 | 4 | 13 | 4 | 0 | 0 | 9 | 0 | 6 | 1 | 3 | 5 | 9 | 6 | 0 |
| 2 | am | 2 | 6 | 14 | 2 | 1 | 3 | 5 | 11 | 7 | 1 | 4 | 5 | 9 | 5 | 0 |

TABLE 3-continued

| | | Saline + Zinc score | | | | | Saline score | | | | | Rinatec score | | | | |
|---|---|---|---|---|---|---|---|---|---|---|---|---|---|---|---|---|
| Day | Time | 0 | 1 | 2 | 3 | 4 | 0 | 1 | 2 | 3 | 4 | 0 | 1 | 2 | 3 | 4 |
| | pm | 3 | 10 | 9 | 3 | 0 | 4 | 10 | 6 | 7 | 0 | 4 | 7 | 7 | 5 | 0 |
| 3 | am | 4 | 9 | 11 | 1 | 0 | 4 | 10 | 6 | 7 | 0 | 3 | 8 | 10 | 1 | 1 |
| | pm | 5 | 9 | 8 | 2 | 0 | 9 | 9 | 5 | 3 | 1 | 3 | 9 | 8 | 3 | 0 |
| 4 | am | 6 | 12 | 4 | 1 | 0 | 6 | 7 | 7 | 3 | 1 | 3 | 11 | 6 | 2 | 0 |
| | pm | 8 | 12 | 2 | 0 | 0 | 7 | 5 | 8 | 0 | 2 | 5 | 10 | 6 | 1 | 0 |
| 5 | am | 7 | 11 | 4 | 0 | 0 | 7 | 5 | 7 | 1 | 1 | 7 | 8 | 5 | 1 | 0 |

1) am and pm denote morning and evening, respectively
2) Scores were assigned as follows:
0 = Not Present
1 = Mild
2 = Moderate
3 = Severe
4 = Very Severe The improvement over the period of the trial for subjects using the spray of the invention is significant. While the commercially available product did not perform noticeably better than the normal saline, an immediate and marked improvement was observed with the product of the invention.

EXAMPLE 2

A preparation of zinc solution (0.1%) was made up in deionized water and placed in individual hand dispensers. Patients having various symptoms of the common cold, ranging from virtually asymptomatic through to streaming nose, were given the dispensers. In each case without exception, rapid relief was experienced after the initial dose of 2 sprays per nostril, each spray being about 0.2 ml. In a number of cases of early infection, the one administration was sufficient to effect a total cure and, in the remainder, 6-hourly doses, as above, offered substantial relief.

What is claimed is:

1. A method for the treatment of the symptoms of the common cold comprising administering a spray of a solution containing a non-toxic, symptom effective treating amount of a solution of a substantially unchelated ionic zinc compound, said solution containing substantially unchelated zinc ions in a concentration of from about 0.004 to about 0.12% (w/vol.), to the nostrils and respiratory tract of a patient in need thereof.

2. The method of claim 1, wherein said solution is selected from the group consisting of aqueous and saline solutions.

3. The method of claim 1, wherein said solution further comprises an effective amount of a flavor and/or odor enhancing agent.

4. The method of claim 1, wherein said solution has an unchelated zinc ion content of about 0.04% (w/v).

5. The method of claim 1 wherein said solution consists essentially of said substantially unchelated ionic zinc compound and at least one pharmaceutically acceptable carrier.

6. The method of claim 1 wherein said substantially unchelated ionic zinc compound comprises a mineral acid salt of zinc.

7. The method of claim 1 wherein said substantially unchelated ionic zinc compound is a salt selected from the group consisting of zinc sulfate and zinc chloride.

8. The method of claim 7 wherein said unchelated ionic zinc compound is zinc sulfate.

* * * * *